United States Patent
Amplatz et al.

(10) Patent No.: US 6,402,772 B1
(45) Date of Patent: Jun. 11, 2002

(54) ALIGNMENT MEMBER FOR DELIVERING A NON-SYMMETRICAL DEVICE WITH A PREDEFINED ORIENTATION

(75) Inventors: Kurt Amplatz, St. Paul; Michael Afremov, St. Louis Park, both of MN (US)

(73) Assignee: AGA Medical Corporation, Golden Valley, MN (US)

( * ) Notice: Subject to any disclaimer, the term of this patent is extended or adjusted under 35 U.S.C. 154(b) by 0 days.

(21) Appl. No.: 09/981,736

(22) Filed: Oct. 17, 2001

Related U.S. Application Data

(62) Division of application No. 09/572,649, filed on May 17, 2000, now Pat. No. 6,334,864.

(51) Int. Cl.[7] .............................................. A61B 17/00
(52) U.S. Cl. ....................................................... 606/200
(58) Field of Search ................................ 606/200, 201, 606/202, 108, 113, 114, 127, 198

(56) References Cited

U.S. PATENT DOCUMENTS

| | | |
|---|---|---|
| 5,334,217 A | 8/1994 | Das |
| 5,522,822 A | 6/1996 | Phelps et al. |
| 5,634,942 A * | 6/1997 | Chevillon et al. .......... 606/200 |
| 5,709,707 A | 1/1998 | Lock et al. |
| 5,725,550 A * | 3/1998 | Nadal .......................... 606/200 |
| 5,725,552 A | 3/1998 | Kotula et al. |
| 5,928,181 A | 7/1999 | Coleman et al. |
| 5,944,738 A | 8/1999 | Amplatz et al. |
| 5,947,428 A | 9/1999 | Ohl |
| 5,960,805 A | 10/1999 | Murphy |
| 5,968,064 A | 10/1999 | Selmon et al. |
| 5,976,174 A | 11/1999 | Ruiz |
| 5,997,536 A | 12/1999 | Osswald et al. |
| 6,004,316 A | 12/1999 | Laufer |
| 6,039,744 A | 3/2000 | Forber |
| 6,126,685 A | 10/2000 | Lenker et al. |

* cited by examiner

*Primary Examiner*—Kevin T. Truong
(74) *Attorney, Agent, or Firm*—Nikolai & Mersereau, P.A.

(57) ABSTRACT

A method for delivering an object within a patient, wherein the object is delivered in a preferred orientation relative to the delivery site of the patient. The delivery device has an alignment member that allows the object to be delivered intravascularly to the delivery site of the patient, wherein the object is delivered in a pre-determined orientation. The object may, for example, be non-symmetric or include a configuration that requires delivery to the site in only one suitable orientation relative to the delivery site. Such objects may be used, for example, to treat certain defects or injuries in vessels or organs within a patient's body.

3 Claims, 5 Drawing Sheets

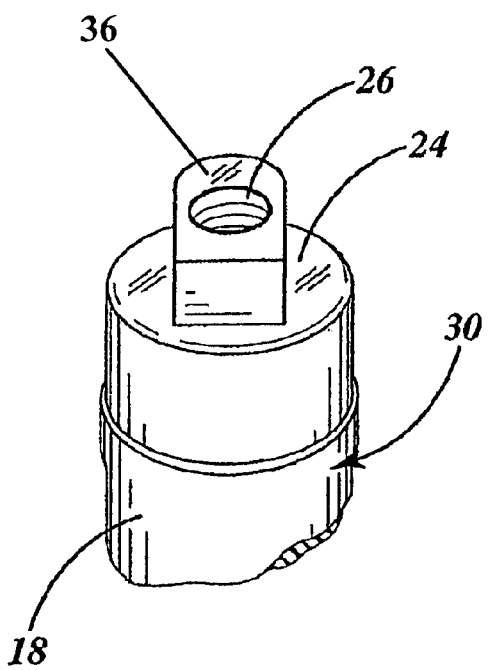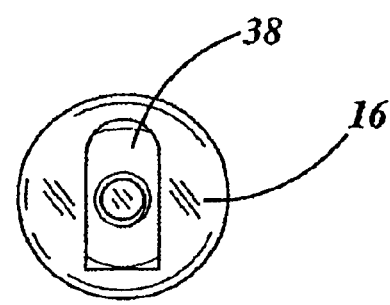
*Fig. 5*  *Fig. 6*
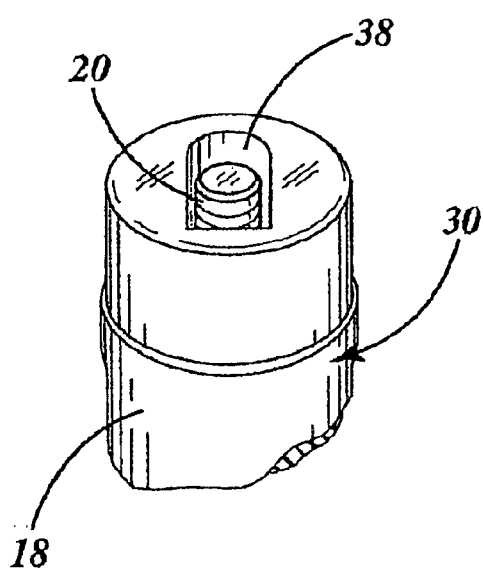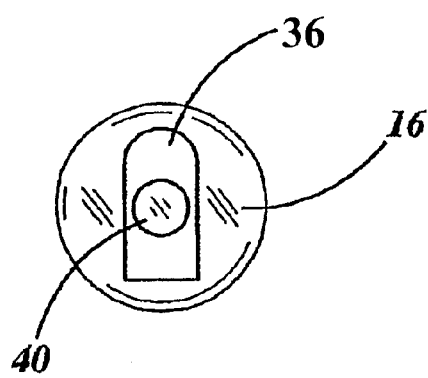
*Fig. 7*  *Fig. 8*

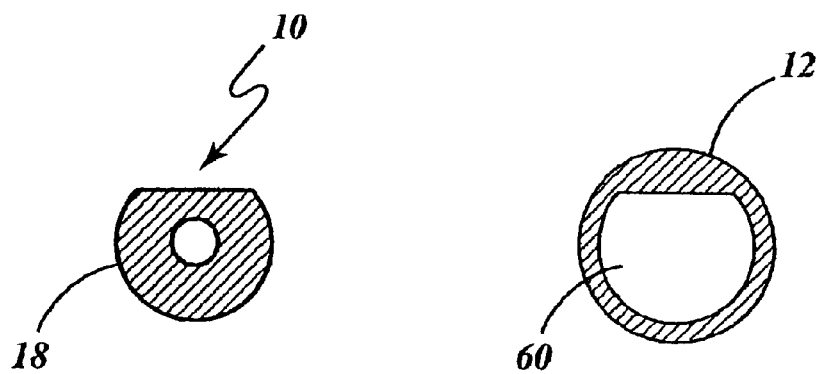
Fig. 9    Fig. 10
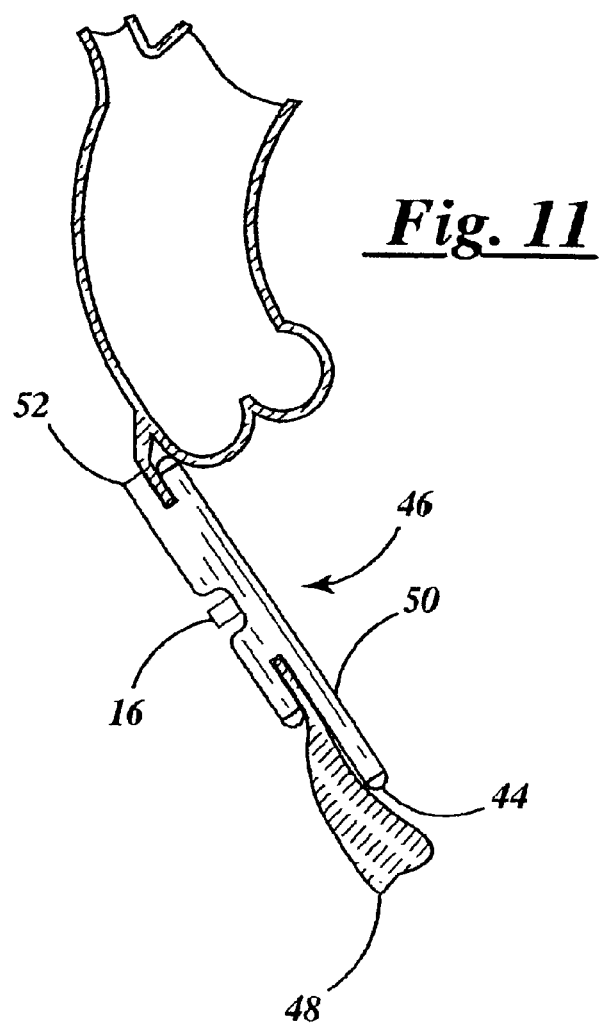
Fig. 11

ALIGNMENT MEMBER FOR DELIVERING A NON-SYMMETRICAL DEVICE WITH A PREDEFINED ORIENTATION

CROSS-REFERENCE TO RELATED APPLICATION

This application is a divisional of prior application Ser. No. 09/572,649, filed May 17, 2000 now U.S. Pat. No. 6,334,864.

FIELD OF THE INVENTION

The present invention relates generally to the delivery of an object within a patient, wherein the object is delivered in a preferred orientation relative to the delivery site of the patient. More particularly, the present invention relates to a delivery device having an alignment member that allows the object to be delivered intravascularly to the delivery site of the patient, wherein the object is delivered in a predetermined orientation. The object may, for example, be non-symmetric or include a configuration that requires delivery to the site in only one suitable orientation relative to the delivery site. Such objects may be used, for example, to treat certain defects or injuries in vessels or organs within a patient's body.

BACKGROUND OF THE INVENTION

Over the years, medical devices delivered intravascularly have been used to treat many types of defects in the tissues and organs of a patient. For example, intra cardiac devices have been used to treat certain congenital defects of the heart including a ventricular septal defect (VSD—a defect or aperture extending through the septum between the left and right ventricles), atrial septal defect (ASD—a defect or aperture extending through the septum between the right and left atrium) or patent ductus arteriosus (PDA—an incomplete closure of an opening between the pulmonary artery and the aorta that is present during fetal development). These conditions may cause blood to abnormally shunt between the heart chambers causing an imbalance in the oxygen levels in the blood causing cyanosis, cardiac enlargement, failure or other complications.

Non-invasive techniques have been developed to treat these defects. These techniques include the use of catheters and guide wires to deliver an occluding device to the desired location within the patient's heart. These devices may be difficult to position and a non-symmetric device may prove to be even further challenging to deliver in a preferred orientation. For example, a PDA device may preferably be shaped non-symmetrically to conform to the angle of the communication between the main pulmonary artery and the aorta. In order for this non-symmetric device to be effective, it must be delivered in the communication with a specific orientation so that the retention disc of the device is flush against the aorta wall. As another example, perimembranous ventricular septal defects are typically very close to the aortic valve. For closure of such defects, the retention mechanism must be asymmetrical wherein the retention disc is offset from the center of the device, such that the retention disc extends further out from the main portion on one side than on the other side of the main portion. The smaller portion of the retention disc or rim is oriented toward the aortic valve.

Other defects in blood vessels, for example, may require the delivery of a device into the vessel, wherein a particular orientation of the device within the vessel is required. For example, the device may include an aperture or some other particular configuration requiring delivery of the device in a particular orientation in the vessel. Hence, there is a need for a device and method of delivering an object to a specific site, wherein the orientation of the object is controlled. The present invention meets these and other needs that should be apparent to those skilled in the art.

SUMMARY OF THE INVENTION

The device of the present invention is suitable for delivering a collapsible object to a pre-selected region within a patient. An elongated pusher catheter, for example, may be modified to include on its distal end a distal tip having an alignment member adapted for mating with a connecting member of the collapsible object. The elongated pusher catheter may further have a preset curve or bend designed to match the shape or curve of the delivery sheath which roughly matches the shape or curve of the vessel adjacent the delivery site. During delivery of the elongated pusher catheter, the catheter tends to rotate so that the bend in the catheter tends towards alignment with the curve in the vessel. When the collapsible object is attached in a fixed position to the distal tip of the elongated pusher catheter, the orientation of the collapsible object is known relative to the bend in the pusher catheter. In this manner, when the elongated pusher catheter is delivered, the orientation of the collapsible object is known relative to the curve of the delivery catheter and the vessel at the delivery site. Correct orientation can be accomplished by incorporating the same curvature in the pusher catheter and the delivery catheter or by preventing rotation of the delivery pusher in the delivery catheter.

In the preferred embodiment the pusher catheter includes a lumen extending there through between the proximal end and distal end, wherein the distal tip includes an aperture extending there through and aligned with the lumen. A cable extends through the lumen of the pusher catheter, wherein a distal end of the cable is extendable through the aperture of the distal tip and coupleable to the collapsible object. Without limitation, the distal end of the cable includes a threaded outer surface and the collapsible object includes a member having a threaded bore adapted for receiving the threaded outer surface of the cable. Those skilled in the art will appreciate that other methods of releaseably fastening objects together may be incorporated into the distal tip and collapsible object without imparting from the present invention.

The distal tip of the pusher catheter further includes an alignment member having a predetermined shape. The coupling member of the collapsible object includes a corresponding mating shape, such that the collapsible object may only align and engage the alignment member in one orientation. For example, without limitation, the shape of the alignment member may be a semicircular, a square with one beveled corner, an isosceles triangle, or other shape that only allows for one mating orientation. The engagement between the alignment member and connecting or coupling member inhibits the collapsible device from rotating about the distal tip.

In use, a non-symmetric object may be delivered within a patient utilizing the device of the present invention, wherein the orientation of the object is predefined. The user first couples the non-symmetric device to an elongated pusher catheter, wherein the distal tip has an alignment member adapted for mating with a connecting member of the non-symmetric device. The device may include a radiopaque marker attached at a predefined position on the asymmetrical device. In this manner, the orientation of the asymmetrical device may be determined through fluoroscopy or another known manner of observation. The orientation of the alignment member is fixed relative to a bend in the pusher catheter. A delivery sheath is then positioned within the patient's body vessel, wherein a distal end of the sheath is proximate a desired site of delivery. The sheath may also have a preset bend corresponding to a shape of the vessel proximate the desired site of delivery. Alternatively, the pusher catheter and interior lumen of the sheath may be shaped to prevent rotation of the pusher catheter within the sheath. The user then loads the non-symmetric device coupled to the pusher catheter into the sheath, by connecting the alignment member in an orientation associated with the curve in the pusher catheter. The pusher catheter is then passed through the sheath until the distal tip of the pusher catheter extends out the sheath. The user may then determine whether the collapsible object has been positioned properly and if desired may disengage the object from the alignment member and tip of the pusher catheter. The user may then remove the pusher catheter and sheath in a known suitable fashion.

BRIEF DESCRIPTION OF THE DRAWINGS

FIG. 5 is a fragmented perspective view of the distal tip of the elongated pusher catheter;

FIG. 6 is a top elevational view of the connecting member of the PDA device shown in FIG. 2;

FIG. 7 is a fragmented perspective view of an alternate embodiment of the distal tip of the elongated pusher catheter;

FIG. 8 is a top elevational view of an alternate embodiment of the connecting member of the PDA device shown in FIG. 2;

FIG. 9 is a sectional view of a pusher catheter;

FIG. 10 is a sectional view showing a shape of the interior lumen of a sheath adapted for receiving a pusher catheter having a shape of the type shown in FIG. 9; and FIG. 11 is a partial sectional side elevational view showing an asymmetrical occluding device positioned in a perimembranous ventricular septal defect.

DETAILED DESCRIPTION

Figure 1:
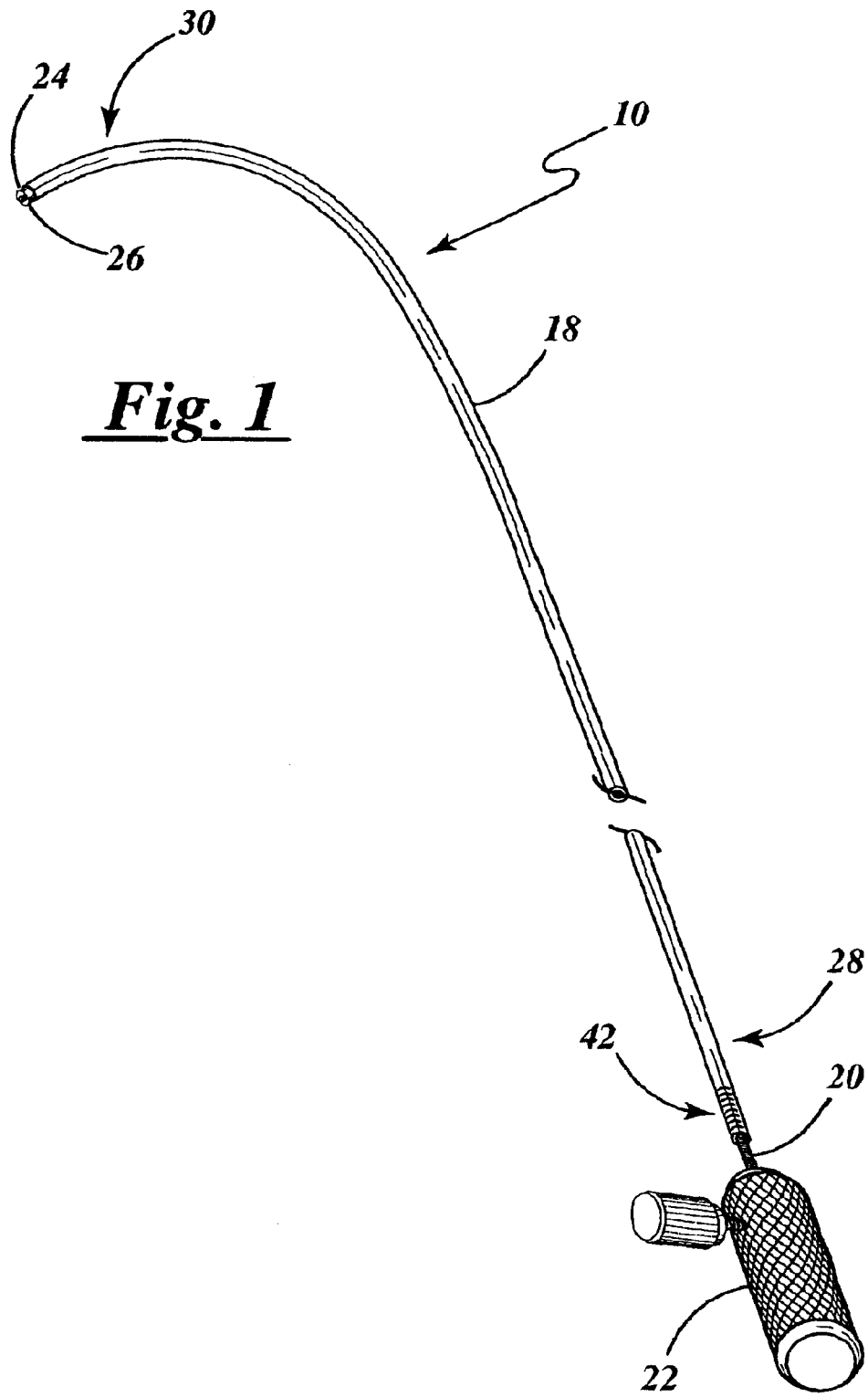
FIG. 1 is a perspective view of the elongated pusher catheter of the present invention.

The following detailed description of the preferred embodiment in conjunction with the accompanying claims and drawings describes the invention in which like numerals in the several views refer to corresponding parts. The present invention represents broadly applicable improvements to a delivery device and methods of delivering an object within a patient in a predetermined orientation. The embodiments detailed herein are intended to be taken as representative or exemplary of those in which the improvements of the invention may be incorporated and are not intended to be limiting.

The present invention provides an elongated pusher catheter 10 deliverable through a sheath 12 and adaptable for coupling a self-expanding object 14 thereto in a predetermined orientation. Without limitation, the self-expanding object 14 has a shape suitable for occluding a PDA, however, those skilled in the art will appreciate that the self-expanding object may be provided in several varying shapes and sizes. For example, the self-expanding object 14 may be configured to be particularly well suited for treating an ASD, VSD, PFO, a triple A graft for the repair of an abdominal aortic aneurysm, or other defect wherein the shape and orientation of the self-expanding object is significant.

Without any limitation intended, the self-expanding object 14 is preferably made from a tubular metal fabric including a plurality of woven metal strands. A clamp 16 is attached to each outer end of metal fabric, thereby inhibiting unraveling of the metal fabric. At least one of the clamps 24 is adapted for coupling to the end of the pusher catheter 10 for delivery to a pre-selected site within the patient, as described below in greater detail.

Once the appropriate self-expanding object 14 has been selected to treat the physiologic condition of the patient, a catheter or other suitable delivery device may be positioned within a channel in a patient's body to place the distal end of the delivery device 10 adjacent the desired treatment site. The delivery device 10 can be used to urge the self-expanding object through the lumen of a sheath or other tube for deployment in a patient's body. When the object is deployed out the distal end of the sheath, the object remains attached to the end of the delivery device. Once it is confirmed that the self-expanding object is properly positioned within the patient, the pusher catheter 10 can be detached from the self-expanding object 14 and then withdrawn. By keeping the self-expanding object 14 attached to the pusher catheter, the operator can retract the object 14 for repositioning, even after deployment out the end of the pusher catheter 10, if it is determined that the object is not properly positioned.

In a preferred embodiment shown in the Figures, the non-symmetric medical occluding self-expanding object 14 is shown attached to the pusher catheter or delivery catheter 10. The pusher catheter 10 generally includes an elongated, flexible, biocompatible tube having a lumen extending along the longitudinal axis. A guide wire or cable may be positioned within the lumen of the pusher catheter, and extends through the tip of the pusher catheter. The tip of the cable is threaded and screws into the end of the clamp, thereby securing the self-expanding object 14 to the pusher catheter 10. The diameter of the lumen within the pusher catheter 10 is dimensioned so that the guide wire may be rotated inside of the pusher catheter 10, yet snug enough to avoid kinking in the cable. The alignment member formed on the tip or distal end of the pusher catheter includes a predetermined shape that mates with a shape formed in the clamp, wherein the alignment member only engages with the clamp in one orientation.

The pusher catheter 10 is curved near its distal tip. The shape of the curve is dependent upon where the particular device is designed to be delivered intravascularly. For example, if the pusher catheter is intended to deliver an occluding device adjacent a PDA, then the curve of the pusher catheter is shaped to approximate the path between the pulmonary artery and communication adjacent the aorta. As will be described below in greater detail, the orientation of the shape fixed within the distal tip may be controlled to thereby affect the orientation of the self-expanding object attached to the alignment member. The curvature of the pusher catheter contributes to the ability of the alignment member to deliver the device in a predefined orientation.

Figure 2:
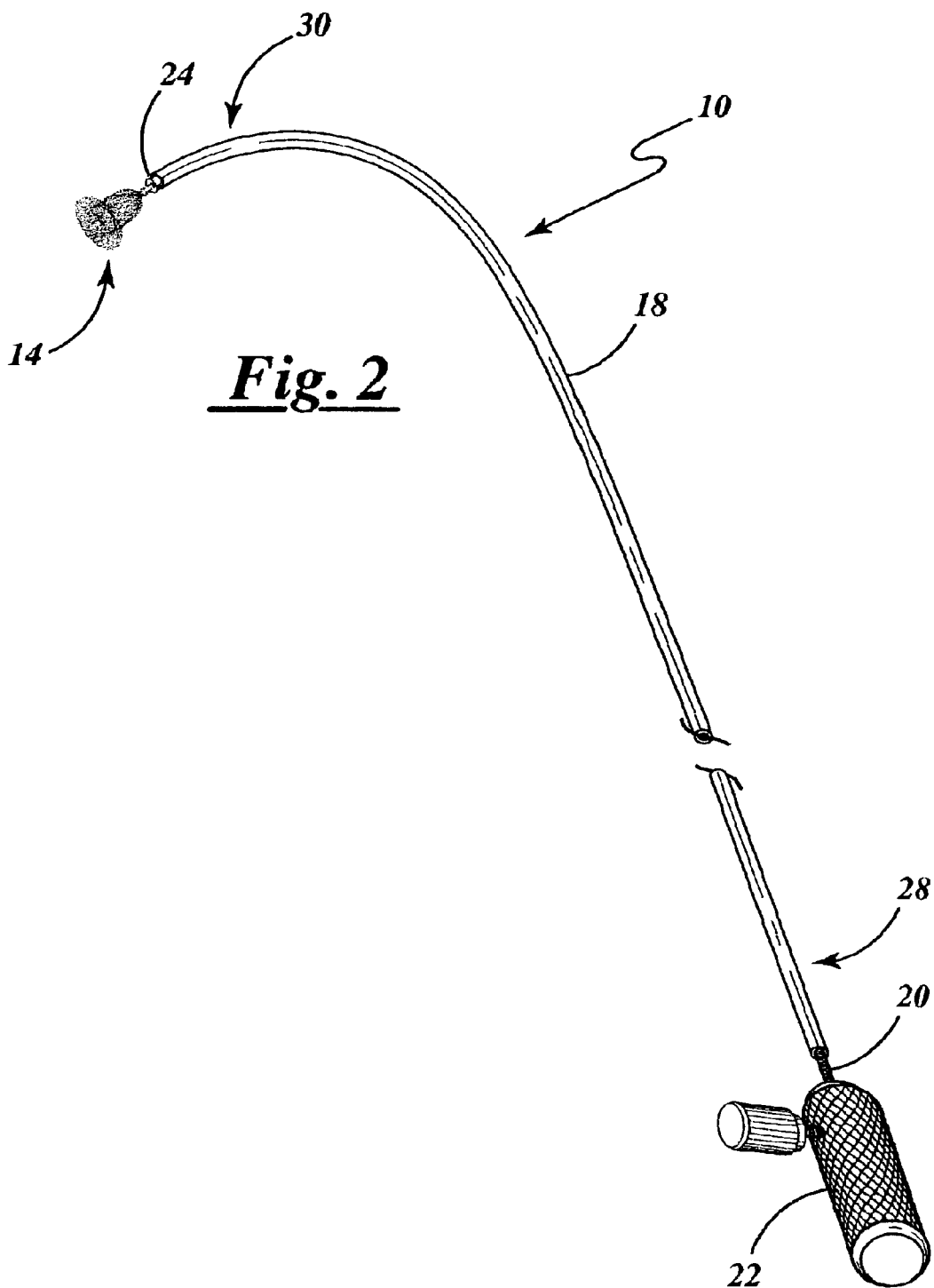
FIG. 2 is a perspective view of the elongated pusher catheter of the type shown in FIG. 1 with a PDA device attached to the distal tip.

Referring now to the Figures, the pusher catheter 10 of the present invention is shown generally in FIGS. 1 and 2. The pusher catheter 10 includes an elongated tubular segment 18 having a proximal and distal end 28 and 30 respectively. A cable 20 extends through the lumen of the tubular segment 18. The distal end 30 of the tubular segment 18 includes an alignment member 24 fixed to the distal end 30 of the tube 18. The alignment member 24 includes an aperture 26 extending there through, wherein the center of the aperture 26 generally aligns with the center of the lumen. The distal end of the cable 20 is threaded and the distal end of the cable extends out the distal end 30 of the tubular segment 18 through the aperture 26 in the alignment member 24. A handle 22 is attached to the proximal end of the cable and assists in the rotation of the cable inside the lumen of the tubular segment 18.

Figure 3:
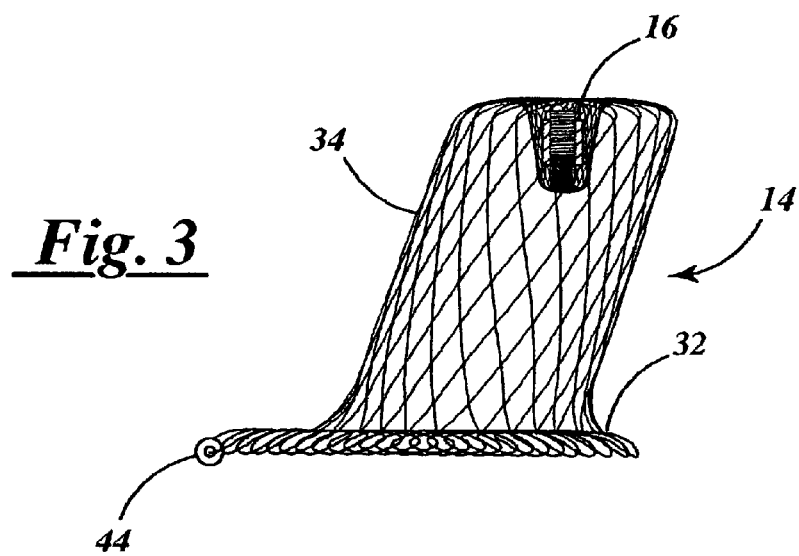
FIG. 3 is side elevational view of the PDA device of the type shown in FIG. 2.
Figure 4:
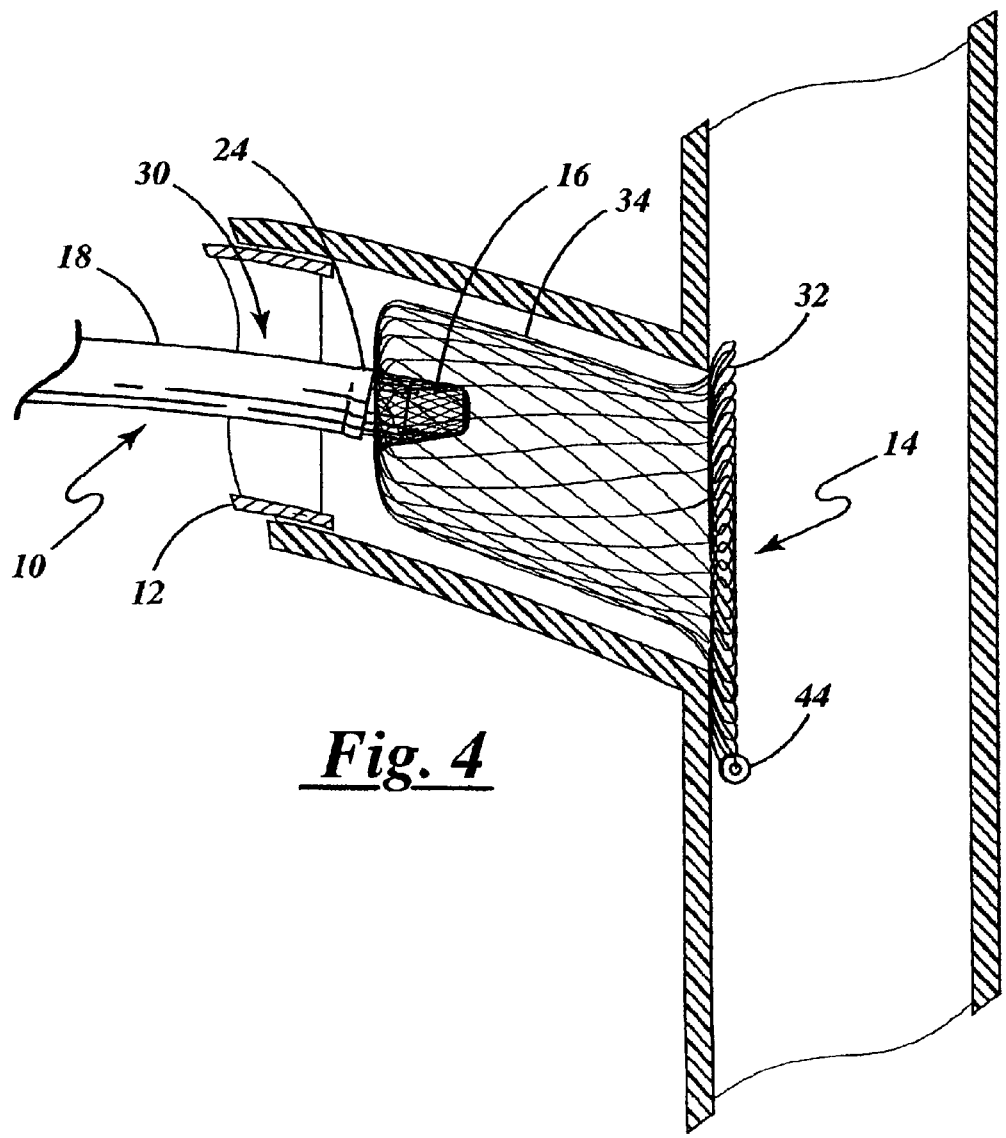
FIG. 4 is a partial sectional side elevational view showing a non-symmetric PDA device being delivered and conforming to the angle of the communication between the main pulmonary artery and the aorta.

FIGS. 2 and 4 show a self-expanding object 14 attached to the pusher catheter 10. The self-expanding object 14 includes a connecting member or clamp 16 that attaches to the alignment member 24 (see FIG. 3). In order to adequately occlude the communication between the aorta and pulmonary artery, the object 14 shown in FIGS. 3 and 4 only has one preferable orientation. The flange, rim or retention disc 32 extends at an acute angle from the main cylindrical portion of the PDA device. In this manner, when the flange 32 rests against the aorta wall, the main cylindrical portion 34 extends into the communication at an angle relative to the longitudinal axis of the aorta proximate the PDA. The non-symmetric object 14 may include a radiopaque marker 44 attached at a predefined position on the asymmetrical device 14. In this manner, the orientation of the asymmetrical device 14 may be determined through fluoroscopy or another known manner of observation.

Referring now to FIGS. 5 and 6, the mating shape of the alignment member 24 and clamp or connecting member 16 is shown. The alignment member 24 includes a protrusion 36 having a semicircular shape on one end of the protrusion 36. The clamp 16 includes a corresponding shape forming a recess 38 formed in the clamp. The protrusion 36 fits within the recess 38 and the distal end of the cable 20 screws into a threaded bore 40 formed in the clamp 16. Alternatively, the protrusion 36 may extend from the clamp 16 and the recess 38 may be formed in the alignment member, as shown in FIGS. 7 and 8. In this manner, the self expanding object 14 may only be attached to the alignment member 24 with one orientation relative to the pusher catheter 10 and, for example, markings 42 on the proximal end of the tube segment 18. Thus, when the object 14 is delivered through the sheath, the orientation of the attached object 14 is known relative to the markings 42. The delivery sheath 12 (see FIG. 4) is positioned within the patient's body vessel, wherein a distal end of the sheath 12 is proximate a desired site of delivery. The sheath 12 may also have a preset bend corresponding to the bend in the pusher catheter 10. Alternatively, the pusher catheter 10 and interior lumen 60 of the sheath 12 may be shaped to prevent rotation of the pusher catheter 10 within the sheath 12 (see FIGS. 9 and 10).

FIG. 11 shows an occluding object 46 positioned to occlude a perimembranous ventricular septal defect in the septum 48. The occluding device 46 is asymmetrical and includes flanges 50 and 52 that engage against the septum 48 and surround the defect. A radiopaque marker 44 is shown attached to flange 50. In this manner, when the occluding device 46 is delivered, the proper positioning of the device 46 may be confirmed. The connecting member 16 mates with the alignment member 24 of the pusher catheter 10. As shown in FIG. 1, the alignment member 24 and connecting member 16 allows for delivery of an asymmetrical device 46 in a preferable orientation, with the longer portion of the flange 52 engaging the septum away from the aortic valve.

This invention has been described herein in considerable detail in order to comply with the patent statutes and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A method for delivering a non-symmetric device within a patient, wherein the orientation of the device is predefined, said method comprising the steps of:

a. coupling a non-symmetric device to an elongated pusher catheter having a proximal end and a distal end, said distal end including a distal tip having an alignment member adapted for non-rotationally mating with a connecting member of the non-symmetric device, wherein the orientation of the alignment member relative to a bend fixed in the pusher catheter is preset;

b. positioning a sheath within the patient's body vessel, wherein a distal end of said sheath is proximate a desired site of delivery, said sheath having a bend fixed therein corresponding to a shape of the vessel proximate the desired site of delivery;

c. loading said non-symmetric device and said pusher catheter into a sheath by orienting said alignment member relative to a curve in said sheath; and d. delivering said non-symmetric device to the desired site.

2. The method of claim 1 and further including the step of:

uncoupling the connecting member of the non-symmetric device from the alignment member following step (d).

3. The method of claim 1 and wherein step (c) further includes stretching the non-symmetrical device to allow the non-symmetric device to fit into a lumen in the sheath.

* * * * *